US012611257B2

(12) United States Patent
Lynch

(10) Patent No.: US 12,611,257 B2
(45) Date of Patent: Apr. 28, 2026

(54) SURGICAL KITS FOR ORTHOPEDIC SURGERY AND ASSOCIATED SURGICAL TECHNIQUES

(71) Applicant: Albert C. Lynch, Landenberg, PA (US)

(72) Inventor: Albert C. Lynch, Landenberg, PA (US)

( * ) Notice: Subject to any disclaimer, the term of this patent is extended or adjusted under 35 U.S.C. 154(b) by 244 days.

(21) Appl. No.: 18/533,605

(22) Filed: Dec. 8, 2023

(65) Prior Publication Data

US 2024/0189035 A1 Jun. 13, 2024

Related U.S. Application Data

(60) Provisional application No. 63/431,643, filed on Dec. 9, 2022.

(51) Int. Cl.
| | |
|---|---|
| *A61B 17/17* | (2006.01) |
| *A61B 17/56* | (2006.01) |
| *A61B 34/10* | (2016.01) |
| *A61B 17/00* | (2006.01) |
| *B33Y 80/00* | (2015.01) |

(52) U.S. Cl.
CPC .............. *A61B 34/10* (2016.02); *A61B 17/17* (2013.01); *A61B 2017/00526* (2013.01); *A61B 2017/568* (2013.01); *A61B 2034/108* (2016.02); *B33Y 80/00* (2014.12)

(58) Field of Classification Search
CPC . A61B 17/151; A61B 17/1775; A61B 17/155; A61B 17/157; A61B 17/158; A61B 2017/565; A61B 2017/568; A61B 2034/102; A61B 2034/105; A61B 2034/108; A61B 34/10; A61B 17/15; A61B 17/152; A61B 17/17; A61B 2017/00526
See application file for complete search history.

(56) References Cited

U.S. PATENT DOCUMENTS

| | | |
|---|---|---|
| 9,421,103 B2 | 8/2016 | Jeng et al. |
| 10,363,149 B2 | 7/2019 | van der Walt et al. |
| 10,398,510 B2 | 9/2019 | Goto |

(Continued)

FOREIGN PATENT DOCUMENTS

| | | |
|---|---|---|
| KR | 101981055 B1 | 5/2019 |

OTHER PUBLICATIONS

International Search Report and Written Opinion from International Application No. PCT/US23/83085 dated Apr. 10, 2024, 11 pages.

*Primary Examiner* — Samuel S Hanna
(74) *Attorney, Agent, or Firm* — Daylight Law, P.C.

(57) ABSTRACT

A method for generating a custom surgical kit for a surgical procedure and associated surgical kits are disclosed herein. The method includes a step of generating a nonconforming bone model of a patient bone. The method includes a step of generating a model of a custom surgical kit for a surgical procedure using the nonconforming bone model. The model of the custom surgical kit includes a set of three contact elements positioned to contact three points of contact on the nonconforming bone model. The set of three contact elements is each statically positioned relative to each other in the model of the custom surgical kit. The method includes a step of producing the custom surgical kit using the model of the custom surgical kit. Further, the method includes a step of positioning the custom surgical kit on the patient bone using the three points of contact.

16 Claims, 6 Drawing Sheets

(56)  References Cited

U.S. PATENT DOCUMENTS

| | | | |
|---|---|---|---|
| 10,675,095 B2 | 6/2020 | Davies et al. | |
| 2010/0082035 A1* | 4/2010 | Keefer .............. | A61B 17/1666 |
| | | | 606/91 |
| 2018/0360609 A1 | 12/2018 | Steines et al. | |

* cited by examiner (i)

(ii)

(iii)

106

102

104

(iv)

(i)

(ii)

(iii)

(i)

(ii)

(iii)

504
506d
506c
506a
506b
502
508

(i)

516b
516a
516c
512
514

518

(iii)

510

(ii)

522
526
524
520

(iv)

524

(v)

600

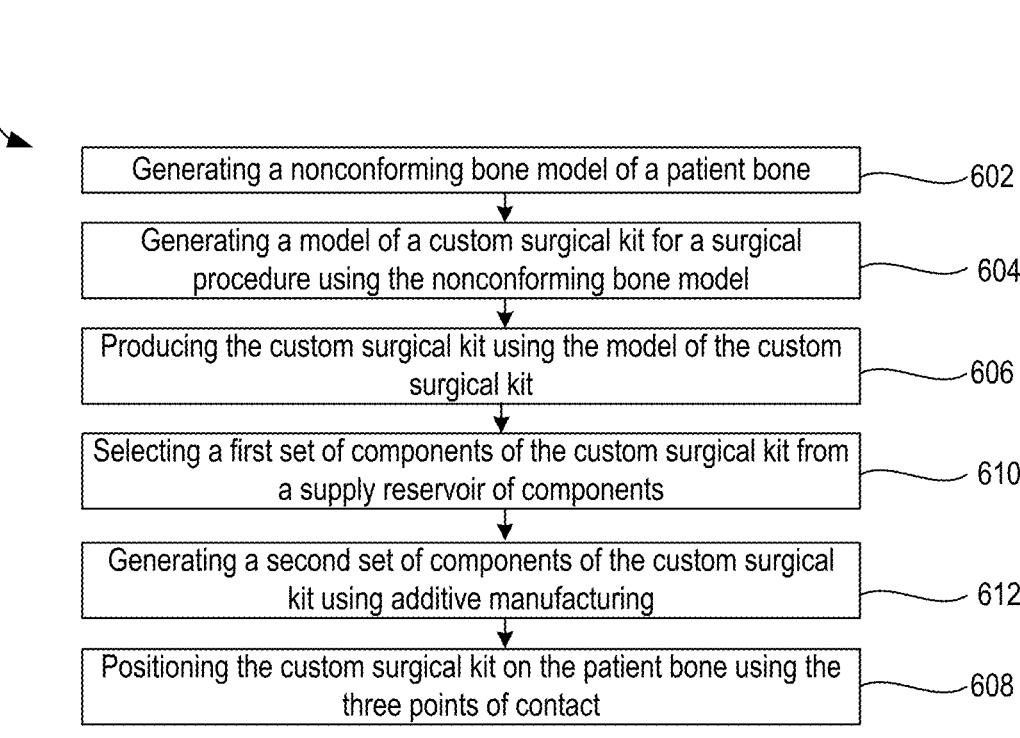

| | |
|---|---|
| Generating a nonconforming bone model of a patient bone | 602 |
| Generating a model of a custom surgical kit for a surgical procedure using the nonconforming bone model | 604 |
| Producing the custom surgical kit using the model of the custom surgical kit | 606 |
| Selecting a first set of components of the custom surgical kit from a supply reservoir of components | 610 |
| Generating a second set of components of the custom surgical kit using additive manufacturing | 612 |
| Positioning the custom surgical kit on the patient bone using the three points of contact | 608 |

FIG. 6

SURGICAL KITS FOR ORTHOPEDIC SURGERY AND ASSOCIATED SURGICAL TECHNIQUES

CROSS-REFERENCE TO RELATED APPLICATIONS

This application claims the benefit of U.S. Provisional Patent Application No. 63/431,643, filed Dec. 9, 2022, which is incorporated by reference herein in its entirety for all purposes.

BACKGROUND

The application of computer modeling and three-dimensional (3D) printing in orthopedics continues to evolve. Traditional uses of such technologies include surgical education, preoperative planning, and procedure rehearsal. Furthermore, the efficacy of intraoperative patient-specific surgical equipment is being reported more commonly. For example, the use of 3D-printed anatomic guides, osteotomy guides, bone alignment guides, and drill guides, as well as other various custom implants, have been demonstrated in vivo. Advantages of these custom surgical instruments specific to a patient's anatomy include improved surgical precision, reduced intraoperative decision-making and surgical duration, and avoidance of harmful intraoperative radiation.

Despite reports of success with patient-specific surgical equipment thus far, several key limitations exist. These limitations include inaccurate modeling of the anatomic features for which the patient-specific surgical equipment is being designed for. The accuracy of 3D-printed anatomic guides that are meant to interface with anatomic features depends on the resolution achieved in source images of those anatomic features. Generally, the source data used for 3D modeling and printing of patient-specific surgical equipment are derived from computed tomography (CT) images. However, the minimum voxel size of conventional CT is orders of magnitude larger than the finely detailed images that modeling and printing software are capable of rendering. This lack of detail can lead to geometric inaccuracy when applied to the generation of patient-specific surgical equipment. CTs are generated using slices of an imaged object where the slice thickness is normally in the range of sub-millimeter to 5-millimeter thick. While attempts to smooth pixelated images in modeling software can help to partially alleviate issues with image slices having larger dimensions, they also have a tendency to further disrupt the geometric accuracy of anatomic landmarks.

The drawbacks associated with inaccurate imaging discussed in the prior paragraph are suffered in addition to the time, radiation exposure, and cost barriers already associated with obtaining CT imaging in the first place. As such, technologies and techniques that minimize, or eliminate, the need for advanced multi-planar imaging in the development of patient-specific surgical equipment are important as they can help to increase the accessibility of patient-specific surgical equipment and associated treatments.

SUMMARY

Methods and systems related to osteosyntheses and associated surgical techniques are discussed herein. In specific embodiments of the invention, methods for generating a custom surgical kit for a surgical procedure and associated surgical kits are provided. In specific embodiments of the invention, methods for accurately positioning a surgical kit with respect to a patient bone and associated custom surgical kits are provided. The methods do not require complex imaging data for determining anatomical landmarks for components of the surgical kit to interface with or the use of fiducials such as K-wires for the placement of components of the surgical kit. In specific embodiments of the invention, a surgical kit including a set of jigs for different phases of a surgical procedure and associated surgical procedures is provided.

In specific embodiments of the invention, a method is provided. The method comprises generating a nonconforming bone model of a patient bone and generating a model of a custom surgical kit for a surgical procedure using the nonconforming bone model. The model of the custom surgical kit includes a set of three contact elements positioned to contact three points of contact on the nonconforming bone model. The method also comprises producing the custom surgical kit using the model of the custom surgical kit. The method also comprises positioning the custom surgical kit on the patient bone using the three points of contact.

In specific embodiments of the invention, a surgical kit is provided. The surgical kit comprises a set of jigs wherein each jig in the set of jigs is configured to facilitate a different phase of a surgical procedure. The jigs can be custom-generated for a unique surgical procedure. The jigs can be generated using additive manufacturing. The surgical kit can also comprise a set of three contact elements positioned to contact three points of contact on a patient. The set of three contact elements includes at least two standoff posts.

BRIEF DESCRIPTION OF THE DRAWINGS

The accompanying drawings illustrate various embodiments of systems, methods, and embodiments of various other aspects of the disclosure. A person with ordinary skills in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 6 is a flowchart of a method for producing a custom surgical kit in accordance with one or more example embodiments.

DETAILED DESCRIPTION

Figure 1:
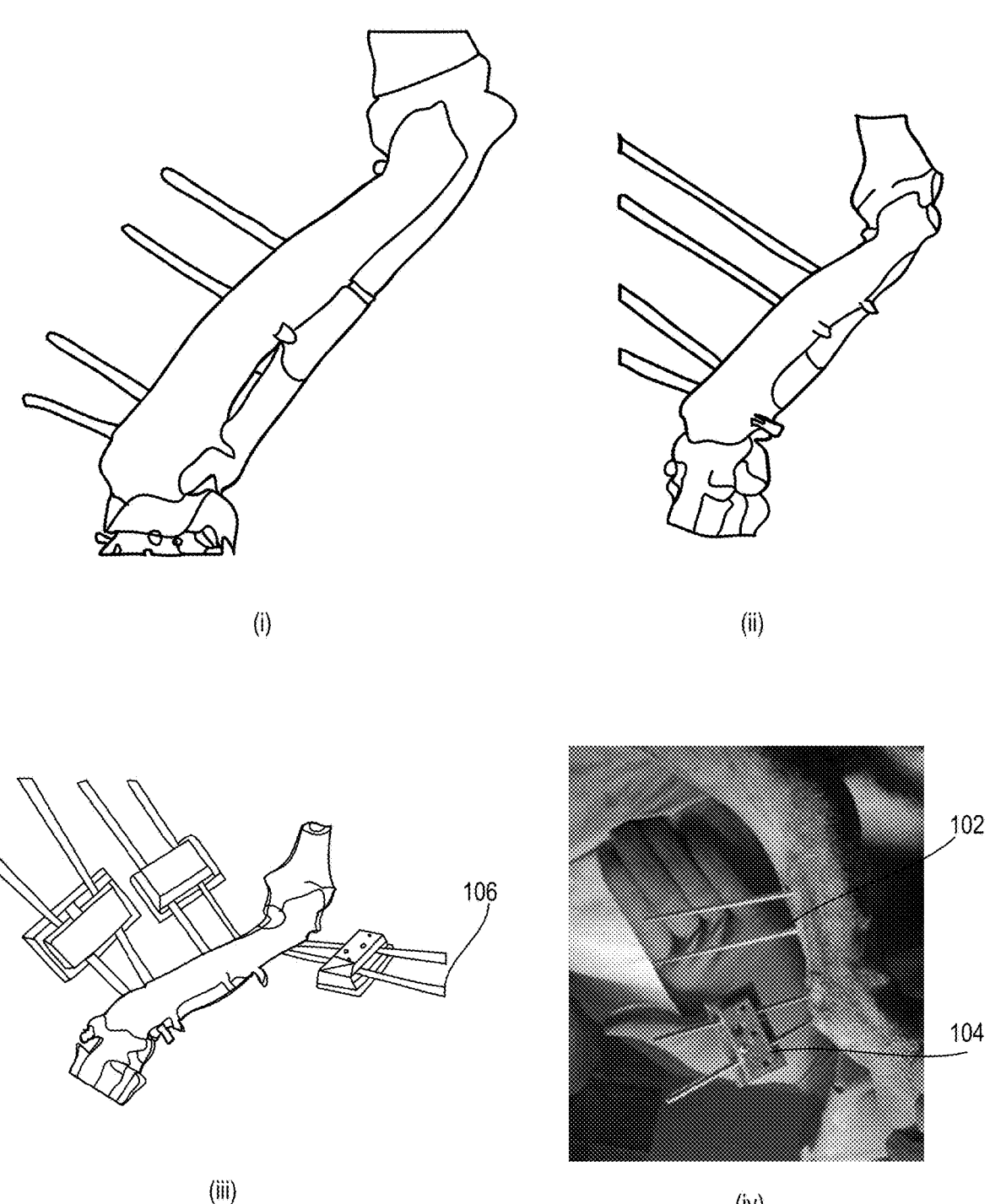
FIG. 1 illustrates an exemplary view of a surgical kit including a plan for a pin placement jig in accordance with one or more example embodiments.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Methods and systems which involve bone models and bone model generators are disclosed in detail herein. The methods and systems disclosed in this section are non-limiting embodiments of the invention, are provided for explanatory purposes only, and should not be used to constrict the full scope of the invention. It is to be understood that the disclosed embodiments may or may not overlap with each other. Thus, part of one embodiment, or specific embodiments thereof, may or may not fall within the ambit of another, or specific embodiments thereof, and vice versa. Different embodiments from different aspects may be combined or practiced separately. Many different combinations and sub-combinations of the representative embodiments shown within the broad framework of this invention, that may be apparent to those skilled in the art but not explicitly shown or described, should not be construed as precluded.

In specific embodiments of the invention, methods for generating a custom surgical kit for a surgical procedure and associated surgical kits are provided. The methods include generating a nonconforming bone model of a patient bone. A bone model of a patient bone can be generated when a patient bone (i.e., a unique patient's bone regardless of gender, age, species, etc.) is nonconforming either due to a deformity, fracture, or other source of anatomical nonconformity. The approaches disclosed herein can utilize a bone model generator engine such as those disclosed with reference to U.S. Pat. App. No. 63/431,093 filed on Dec. 8, 2022, and U.S. patent application Ser. No. 18/533,504 filed on Dec. 8, 2023, which are both incorporated by reference in their entirety herein for all purposes. The surgical kit components disclosed herein can include the local and global jig elements disclosed in U.S. patent application Ser. No. 15/937,842 filed Mar. 27, 2018, and incorporated by reference in its entirety herein for all purposes. In accordance with specific embodiments disclosed herein, the nonconforming bone model can be generated from standard radio orthographs and no other imaging data of the patient bone. The model can be generated without complex imaging systems such as CT imaging systems.

The methods also include generating a model of a custom surgical kit for a surgical procedure using the nonconforming bone model. The model of the custom surgical kit includes a set of three contact elements positioned to contact three points of contact on the nonconforming bone model. The points of contact can be on the surface of the bone or on the surface of the skin. The points of contact can be sufficiently separated such that when they are contacted by contact elements having fixed positions relative to a chassis of a surgical kit, the chassis is uniquely localized with respect to the bone. In this regard, the bone model can also include a model of the position of the surface of the patient's skin relative to the bone. The three contact elements can be statically positioned in the set of three contact elements. This means that the three contact elements are in fixed positions relative to each other in the surgical kit by, for example, all being connected to the same chassis and having fixed poses relative to the chassis. If the model has been generated correctly, the bone is in one continuous fixed piece, and the contact elements are in fixed positions relative to each other, then aligning the three contact elements with three points of contact on the nonconforming bone model will ensure, via triangulation, that the surgical kit is positioned as expected relative to the bone.

The contact elements can be configured to be fixed points of contact or unfixed points of contact. As an example of unfixed points of contact, the points of contact can include standoff points (e.g., at least two) and the contact element can be a set of two standoff posts that are designed to contact and rest upon the two standoff points. A standoff point can be a point on the patient's skin or the surface of the bone on which the standoff posts can rest. As an example of a fixed point of contact, the points of contact can include a pin connected to a pin target (e.g., at least one) and the set of contact elements can include a pin holder that holds the pin that is connected to the pin target.

The methods also include producing the custom surgical kit using the model of the custom surgical kit. The surgical kit can include various components. The components can include contact elements such as the standoff posts and pin holders mentioned above, pins for the pin holders, various jigs, and other elements. The pin holders and various jigs can be connected to the chassis mentioned above. In specific embodiments, the jig and chassis will be the same element (e.g., in a surgical kit having a single jig that is triangulated with respect to the patient and then used throughout the surgical procedure).

Portions of the surgical kit, such as a first set of components, can be selected from a supply reservoir of components. The supply reservoir can contain a selection of components with different variations in terms of their size, shape, and purposes. The components selected from the supply reservoir can be modular to interface with other sets of components having different sizes and purposes. The components can include modular connectors for interfacing with other components of the surgical kit such as components of the second set of components mentioned below. For example, the pin holders and standoff posts can be modular and be designed to interface with interfaces on other components in the surgical kit such as jigs. The modular interfaces can include snap connections, friction bonds, screws, adhesives, or various other means.

Portions of the surgical kit, such as a second set of components, can be custom-generated on demand for a specific surgical kit. For example, the second set of components can be generated using additive manufacturing processes such as three-dimensional printing. The second set of components can be custom generated for a unique surgical procedure such as a specific surgery to translate a given bone into conformity or to perform an osteotomy to correct a bone deformity. The second set of components can include a jig or set of jigs for the surgical kit. The jig or set of jigs can be configured to interface with the modular components. The jig or set of jigs can also be configured to fix the contact elements and statically position the contact elements in the set of contact elements. For example, the jig could be a rigid element, and the contact elements could all be rigidly and fixedly attached to the jig with a fixed pose relative to the jig. The jigs could also be configured to only connect to other jigs in a single position to localize each added jig with respect to the jig or jigs to which it was being attached.

The jigs can be used for various reasons. The jig or set of jigs can include a cutting guide used to guide an incision by a surgeon during a surgical procedure. The surgical kit can include a set of jigs that are used for different purposes such as for pin placement, for guiding an incision, for translating bone segments, and for other reasons. The surgical kit can include a set of jigs where the jigs in the set of jigs are introduced in the surgical procedure, in turn, in each phase of the surgical procedure. For example, the set of jigs could include a first pin alignment jig used in a first phase, a cutting guide jig used in a second phase in which the bone is cut, and a translation guide jig used in a third phase in which the bone is translated. As another example, the set of jigs could include a drill guide jig used in a bone plate alignment phase to guide the drilling of bone screws into the bone in the last phase of a surgical procedure. The set of jigs could be assembled into a single jig in a first step of the surgical procedure. Alternatively, the jigs in the set of jigs could be added or taken away from the main assembly in sequence as the surgical procedure was taking place. For example, each jig in the set of jigs could be configured to facilitate a different phase of a surgical procedure and be added to the overall assembly when that phase of the surgical procedure was about to commence. In these embodiments, the jigs from prior phases could either be kept in place as additional jigs were added, or the jigs from prior phases could be removed and replaced.

In specific embodiments of the invention, the jigs could include visual alignment labels in order to assist in their addition to the main assembly. The jigs could also include labels to indicate which phase of a surgical procedure they were utilized in. The jigs could also include labels indicating how different surgical procedures should be conducted such as by indicating a size or type of compatible pin for a pin guide or a characteristic of a cutting tool for an incision. In embodiments in which the jigs are custom generated, such as via additive manufacturing, the labels could be generated using the same process. For example, the labels could appear as raised portions of a jig printed using a three-dimensional printer. A set of jigs generated in accordance with specific embodiments of the invention disclosed herein could thereby include visual alignment labels generated with the jigs using additive manufacturing.

In specific embodiments of the invention, a surgical kit can include a pin alignment jig. The pin alignment jig can be attached to a portion of the surgical kit that is already in contact with three points of contact on the patient. A set of jigs for a surgical procedure can include a first jig used in a first phase, the first jig can include at least one pin alignment hole. For example, the pin alignment jig can connect to a jig that is already connected to three pins that are attached to a bone of the patient. The pin alignment jig can thereby be uniquely localized with respect to the patient's bone. The pin alignment jig can include at least one pin alignment hole to receive a pin for the addition of additional pins to the patient's bone at specific locations which are defined based on the unique localization of the pin alignment jig. This additional pin, or pins, can be in addition to a set of three contact elements that were used to localize the pin alignment jig, or the jig to which the pin alignment jig was attached. In alternative embodiments of the invention, the pin alignment jig can include sockets for three or more pins and can fix the pins at specific poses and locations relative to the pin alignment jig. The pin alignment jig can then serve to anchor three contact elements, in the form of the at least three pins, for contacting the patient.

In specific embodiments of the invention, a pin alignment jig can be added to an existing jig in order to add pins to a portion of a bone that will be separated during a surgical procedure. For example, the pins could be added to a portion of a bone on one side of a planned osteotomy site that is on the opposite side of the site from pins that have already been used to contact the bone and localize the pin alignment jig with respect to the bone. In specific embodiments of the invention, a model of a custom surgical kit being used to generate a surgical kit for a surgical procedure can include a model of a pin for a pin alignment hole in a pin alignment jig. The model of the pin can contact a portion of the nonconforming bone model and the portion of the nonconforming bone model can model a portion of the patient bone that will be separated from the patient bone in the surgical procedure.

As the jigs in the surgical kit may be made of plastic or some other material capable of use in inexpensive additive manufacturing, the surgical kit can include a cutting and/or drill guide shield to prevent damage to the cutting and/or drill guide during the incision. The cutting guide could be metal or some other material that was relatively strong compared to the material of the cutting guide. The cutting guide could also be selected from a supply reservoir of components. The model of the surgical kit could be designed to accommodate a specific cutting guide shield proximate to the cutting guide.

A first example in accordance with specific embodiments of the invention disclosed herein is provided in FIG. 1 that illustrates an exemplary view of a surgical kit including a plan for a pin placement jig, in accordance with one or more example embodiments. In the example of FIG. 1, placement of the initial pins is conducted using fiducials in the form of K-wires, but the overall surgical kit represented by this example is still in accordance with the embodiments disclosed herein. Regarding pin placement, K-wires initially utilized for reference registration (as shown in (i) of FIG. 1) are modeled by modeled Steinmann pins (as shown in (ii) of FIG. 1). These virtual pins match the size of pin 102 that will be utilized at surgery (as shown in (iv) of FIG. 1 to attach to the pin set handle (104). The pin set handle 104 in this case is an example of a jig in a surgical kit. As shown in (iii) of FIG. 1, a third pin set is required for the surgical procedure that had no reference K-wire pin set present and was therefore modeled virtually 106 for future insertion via a pin placement jig.

Figure 2:
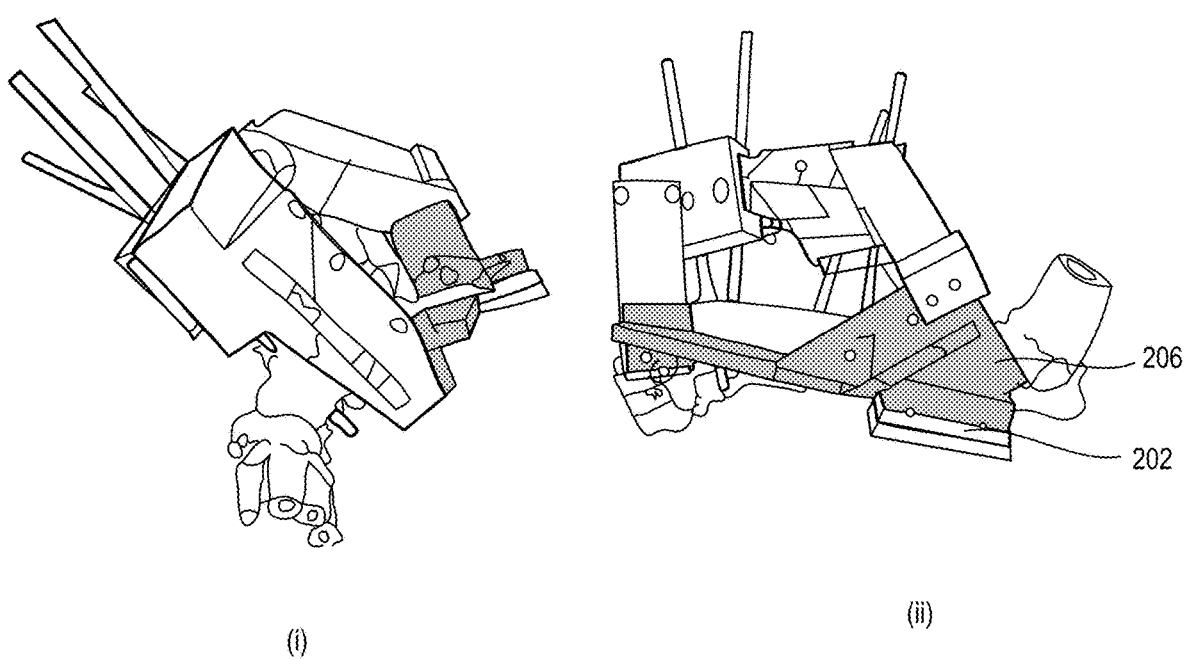
FIG. 2 illustrates additional jigs added for different phases of surgical procedure in accordance with one or more example embodiments.
Figure 2:
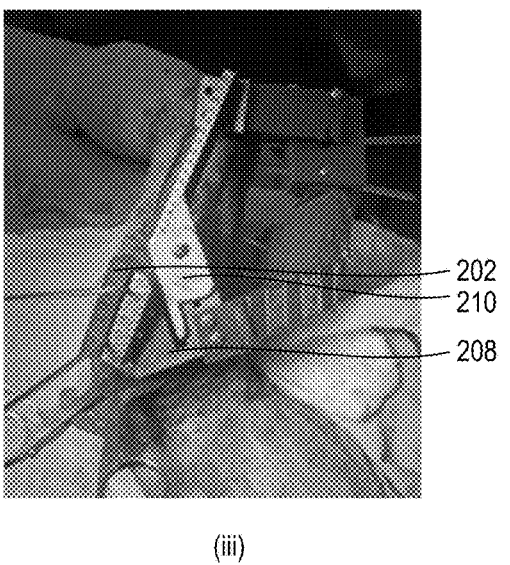

FIG. 2 continues the example from FIG. 1 with the next phase of the surgical procedure. FIG. 2 illustrates additional jigs added for different phases of surgical procedure, in accordance with one or more example embodiments. As seen, additional jigs have been connected to the local jigs attached to the pins in FIG. 1. The additional jigs include a cut guide and pin alignment holes. The pin alignment holes are for additional pins and the cut guide provides a guide for where the bone should be cut during the osteotomy. The pin guides are needed to insert pins into the portion of the bone that will be severed during that osteotomy. As illustrated, a rigid pin placement jig to secure all three pin handles and corresponding pin sets is modeled (as shown in (i) and (ii) of FIG. 2) and utilized in surgery (shown in (iii) of FIG. 2). The images also show the location where the third pin set was modeled 202 and successfully placed at surgery. The pin placement jig also had cutting guides modeled 206 that were enclosed on at least three sides and can be seen at surgery 208. The figures also illustrate a metal shield 210 that was secured to the cutting guide to avoid any fragments from the jig components being formed during surgery.

Figure 3:
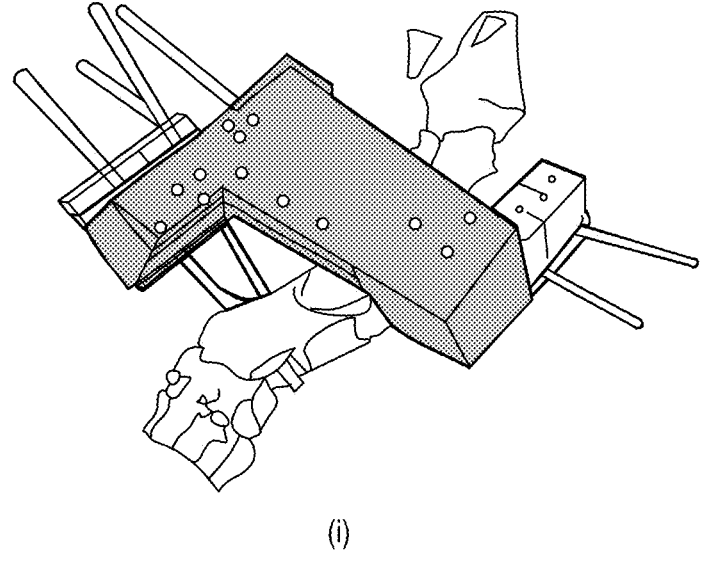
FIG. 3 illustrates a perspective view of a final alignment jig, in accordance with one or more example embodiments.
Figure 3:
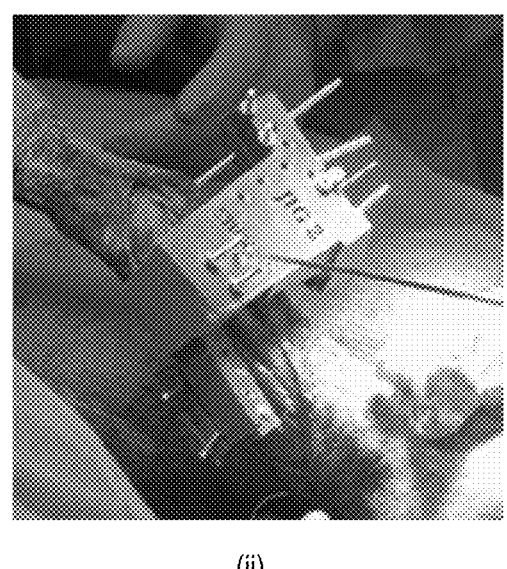
Figure 3:

FIG. 3 continues the example from FIG. 2 with the next phase of the surgical procedure. FIG. 3 illustrates a perspective view of a final alignment jig, in accordance with one or more example embodiments. As seen, a final alignment jig and implant guide are used to align the bone segments after the osteotomies. The pin placement jig is removed and replaced with the final alignment jig, which also has implant guides (i.e., drill guides in this case) to guide the process of securing a bone plate to the bone segments. The final alignment jig may be seen as modeled (as shown in (i) of the FIG. 3) and in surgery (as shown in (ii) of the FIG. 3), as well as in a post-operative lateral radiograph (as shown in (iii) of FIG. 3).

Figure 4:
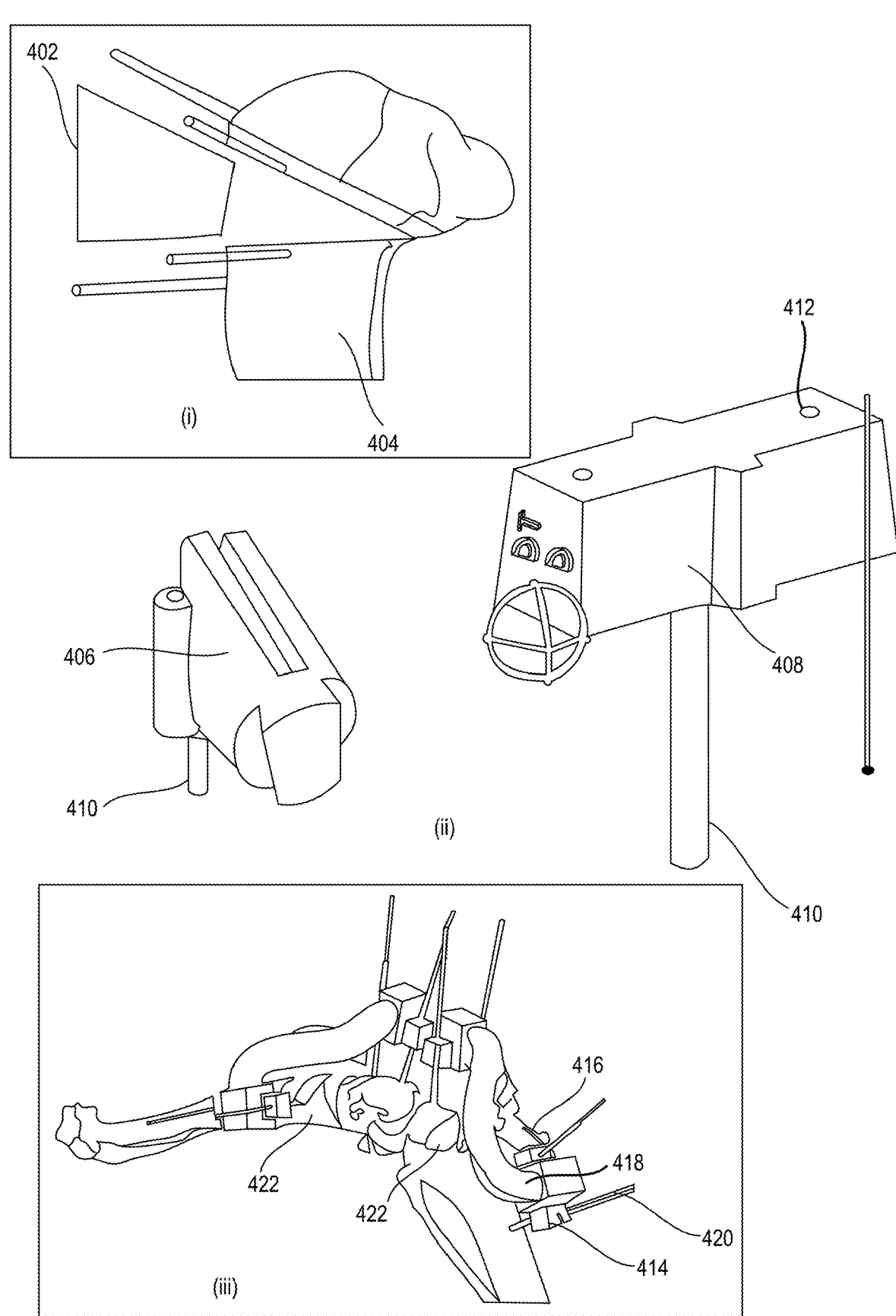
FIG. 4 illustrates a perspective view of a jig placement without fiducials in accordance with one or more example embodiments.

A second example in accordance with specific embodiments of the invention disclosed herein is provided in FIG. 4 which shows an example of how a surgical kit can be placed on a patient using three points of contact and without complex imaging or fiducials. FIG. 4 illustrates a perspective view of a jig placement without fiducials, in accordance with one or more example embodiments. In the example of FIG. 4, the true magnitude of the deformity is propagated in the true plane of the deformity to automatically generate a basic osteotomy cutting guide 402. As illustrated, locoregional pin placement 404 is also automatically determined in the modeling software. Both the pin placement and complexity of the cutting guide may be altered by the operator depending on needs and preferences. FIG. 4 also shows a cutting guide 406 and pin handle 408 as seen with their stand-off guides 410 to ensure precision spatial relation to the bone's surface, and subsequent pin set insertion. Pin handle 408 additionally includes a pin hole 412 for providing alignment for a pin for that is to be inserted into a bone. In the figure, the cutting guide is enclosed on three sides, and a pin guide on the cutting guide is seen. Both components have drafted dove tail slots, affording them modular mating capability. The components also include labels which help ensure proper modular mating and orientation. The entire component assembly is seen for the pin placement jig. Pin handles such as pin handle 414, cutting guides such as cutting guide 416, pin placement jig 418, and pins 420 are shown with the pins being inserted to support either side of the joint after the osteotomy of the surgery is completed. Planned closing wedge ostectomy sites 422 of the femur and tibia are also shown.

Figure 5:
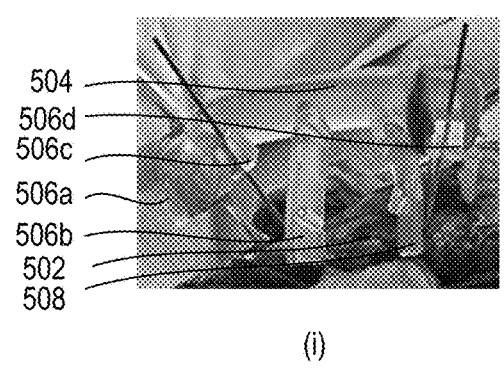
FIG. 5 illustrates a sequence of photographs captured from a surgical procedure in accordance with one or more example embodiments.
Figure 5:
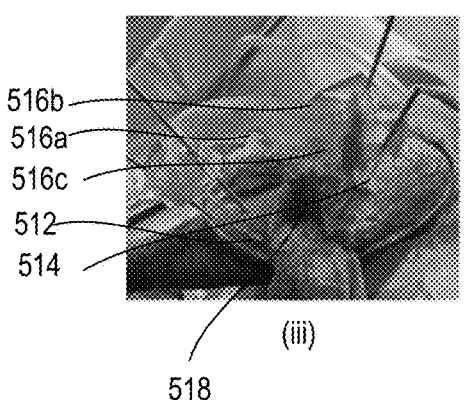
Figure 5:
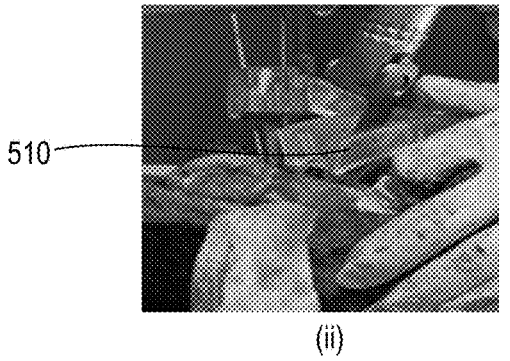
Figure 5:
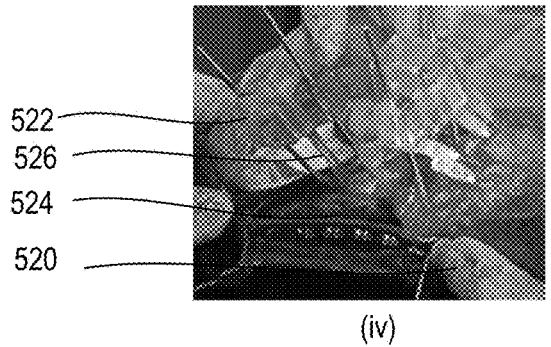
Figure 5:
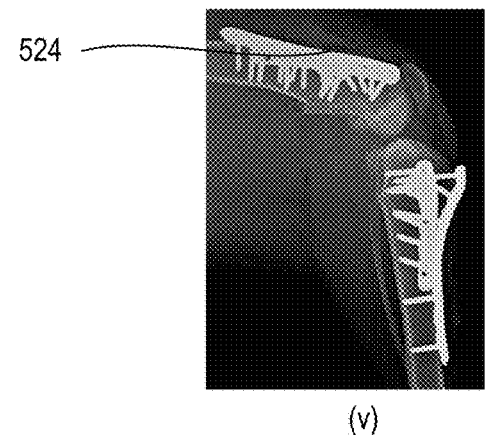

The example of FIG. 4 is further explored in FIG. 5 that illustrates a sequence of photographs captured from the surgical procedure performed in accordance with this example and a post-operative lateral radiograph. FIG. 5 includes, in section (i), patient bone 502, pin placement jig 504, pin handles 506*a*, 506*b*, 506*c*, and 506*d* and cutting guides 508. Pin handles 506*a*, 506*b*, and 506*d* are modular. In specific embodiments, some pin handles can be modular while others are custom elements, and some pin handles can be removable from a jig while others are integrated parts of the jig. As illustrated, pin handle 506*b* is an integrated part of placement jig 504. FIG. 5 also includes, in section (ii), a photograph of the use of a cutting guide 510 at surgery. FIG. 5 also includes, in section (iii), patient bone 512, pins and pin handle 514, the site of detached cutting guides 516*a*, 516*b*, and 516*c*, and excised bone section 518. FIG. 5 also includes, in section (iv), patient bone 520 and final alignment jig 522 translating the bone to a desired end position. FIG. 5 also includes, in section (v), a radiograph of a patient tibia and femur showing desired alignment and osteotomy apposition along with internal fixation devices. Sections (iv) and (v) both show internal fixation implant 524. A standoff post 526 in accordance with embodiments of this disclosure can also be seen in section (iv).

FIG. 6 is a flowchart of method 600 for producing a custom surgical kit, in accordance with one or more example embodiments. Method 600 includes a step 602 of generating a nonconforming bone model of a patient bone. In an embodiment, the nonconforming bone model is generated using standard radio orthographs and no other imaging data of the patient bone. Method 600 then includes a step 604 of generating a model of a custom surgical kit for a surgical procedure using the nonconforming bone model. The model of the custom surgical kit can include a set of three contact elements positioned to contact three points of contact on the nonconforming bone model. The three contact elements in the set of three contact elements can each be statically positioned relative to each other in the model of the custom surgical kit.

Method 600 includes a step 606 of producing the custom surgical kit using the model of the custom surgical kit. Further, the method 600 includes a step 608 of positioning the custom surgical kit on the patient bone using the three points of contact. In an embodiment, the three points of contact include at least two standoff points. In an embodiment, the set of three contact elements includes at least two standoff posts that are designed to contact the at least two standoff points. In an embodiment, the at least two standoff posts have modular connectors for interfacing with different elements of the custom surgical kit. In an embodiment, the three points of contact include a pin target; and the set of three contact elements includes a pin holder and a pin. The pin holder holds the pin and the pin is connected to the pin target. In an embodiment, the pin holder has modular connectors for interfacing with different elements of the custom surgical kit.

In specific embodiments, the surgical kit can be made of components that are drawn from a supply reservoir of available components. In specific embodiments, the surgical kit can also include components that are custom made for an individual patient. These custom components can be generated using various processes such as additive manufacturing. As such, method 600 of producing the custom surgical kit includes step 610 of selecting a first set of components of the custom surgical kit from a supply reservoir of components. In an embodiment, the first set of components of the custom surgical kit includes modular pin holders, modular standoff posts, and bone pins, and the second set of components of the custom surgical kit includes a set of jigs. In an embodiment, the set of jigs includes a cutting guide, and the first set of components includes a metal cutting guide shield. Furthermore, method 600 includes step 612 of generating a second set of components of the custom surgical kit using additive manufacturing. In an embodiment, the second set of components includes a set of jigs, and the jigs in the set of jigs include visual alignment labels generated with the jigs using additive manufacturing.

In an embodiment, the custom surgical kit includes a first jig. The first jig is positioned relative to the patient bone by the set of three contact elements. The first jig includes at least one pin alignment hole to receive a pin. The pin is not in the set of three contact elements. In an embodiment, the custom surgical kit includes a set of jigs. Each jig in the set of jigs facilitates a different phase of a set of different phases of the surgical procedure. In an embodiment, the set of jigs includes a first jig used in a first phase, and the first jig includes a pin alignment hole. In an embodiment, the model of the custom surgical kit includes a model of a pin for the pin alignment hole. The model of the pin contacts a portion of the nonconforming bone model. The portion of the nonconforming bone model models a portion of the patient bone that will be separated from the patient bone in the surgical procedure. In an embodiment, the jigs in the set of jigs are introduced in the surgical procedure, in turn, in each phase of the set of different phases. In an embodiment, the set of jigs includes a pin alignment jig used in a first phase, a cutting guide jig used in a second phase, and a translation guide jig used in a third phase. In an embodiment, the set of jigs includes a drill guide jig used in a bone plate alignment phase.

According to an embodiment herein, a custom surgical kit is provided that includes a set of jigs, wherein each jig in the set of jigs is configured to facilitate a different phase of a surgical procedure. In an embodiment, the set of jigs are custom generated for a unique surgical procedure, and the set of jigs are generated using additive manufacturing. In an embodiment, the custom surgical kit further includes a set of three contact elements positioned to contact three points of contact on a patient's bone. The set of three contact elements includes at least two standoff posts.

While the specification has been described in detail with respect to specific embodiments of the invention, it will be appreciated that those skilled in the art, upon attaining an understanding of the foregoing, may readily conceive of alterations to, variations of, and equivalents to these embodiments. Any of the method steps discussed above can be conducted by a processor operating with a computer-readable non-transitory medium storing instructions for those method steps. The computer-readable medium may be a memory within a personal user device or a network-accessible memory. Although examples in the disclosure were generally directed to bone model generation for supporting surgeries, the bone models generated using the approaches disclosed herein could be applied to numerous other applications such as for product prototyping, educational purposes, and other applications. These and other modifications and variations to the present invention may be practiced by those skilled in the art, without departing from the scope of the present invention, which is more particularly set forth in the appended claims.

What is claimed is:

1. A method, for producing a surgical kit, comprising:
generating, using bone model generating instructions stored in a computer-readable medium, a nonconforming bone model of a patient bone wherein the nonconforming bone model is generated using x-ray images of the patient bone in two orthographic planes and without computed tomography images of the patient bone, and wherein the patient bone is a tibia or a femur;
generating, using surgical kit generating instructions stored in a computer-readable medium, a model of a custom surgical kit for a surgical procedure using the nonconforming bone model, wherein the model of the custom surgical kit includes a set of three contact elements positioned to contact three non-collinear points of contact on the nonconforming bone model, wherein the set of three contact elements are each statically positioned relative to each other in the model of the custom surgical kit;
producing the custom surgical kit using additive manufacturing and the model of the custom surgical kit, wherein the custom surgical kit includes a cutting guide, and wherein the surgical kit comprises three statically fixed contact elements arranged to contact the three non-collinear points on the patient so as to uniquely localize the surgical kit in three-dimensional space without surface conformity;
positioning the custom surgical kit on the patient bone using the three non-collinear points of contact; and
cutting the patient bone using the cutting guide to perform an osteotomy;

wherein the custom surgical kit includes pin holders, standoff posts, bone pins, and a set of jigs.

2. The method of claim 1, wherein producing the custom surgical kit comprises: selecting a first set of components of the custom surgical kit from a supply reservoir of components, wherein the supply reservoir includes a selection of components with different variations in terms of their size, shape, and purpose; and
generating a second set of components of the custom surgical kit using the additive manufacturing.

3. The method of claim 2, wherein: the first set of components of the custom surgical kit includes the pin holders, the standoff posts, and the bone pins; and the second set of components of the custom surgical kit includes the set of jigs.

4. The method of claim 3, wherein: the set of jigs includes the cutting guide; and the first set of components includes a metal cutting guide shield.

5. The method of claim 3, wherein: the jigs in the set of jigs include visual alignment labels generated with the jigs using additive manufacturing.

6. The method of claim 1, wherein:
the three non-collinear points of contact include at least two standoff points; and
the set of three contact elements includes at least two standoff posts that are designed to contact the at least two standoff points.

7. The method of claim 6, wherein the at least two standoff posts have modular connectors for interfacing with different elements of the custom surgical kit.

8. The method of claim 1, wherein: the three non-collinear points of contact include a pin target; and the set of three contact elements includes a pin holder and a pin, wherein the pin holder holds the pin and the pin is connected to the pin target.

9. The method of claim 8, wherein the pin holder has modular connectors for interfacing with different elements of the custom surgical kit.

10. The method of claim 1, wherein: the custom surgical kit includes a first jig; the first jig is positioned relative to the patient bone by the set of three contact elements; the first jig includes at least one pin alignment hole to receive a pin; and the pin is not in the set of three contact elements.

11. The method of claim 1, wherein: each jig in the set of jigs facilitates a different phase of a set of different phases of the surgical procedure.

12. The method of claim 11, wherein: the set of jigs includes a first jig used in a first phase; and the first jig includes a pin alignment hole.

13. The method of claim 12, wherein: the model of the custom surgical kit includes a model of a pin for the pin alignment hole; the model of the pin contacts a portion of the nonconforming bone model; and the portion of the nonconforming bone model models a portion of the patient bone that will be separated from the patient bone in the surgical procedure.

14. The method of claim 11, wherein the jigs in the set of jigs are introduced in the surgical procedure, in turn, in each phase of the set of different phases.

15. The method of claim 11, wherein;
the set of jigs includes: a pin alignment jig used in a first phase;
a cutting guide jig used in a second phase; and a translation guide jig used in a third phase; and
wherein the cutting guide jig is the cutting guide.

16. The method of claim 11, wherein the set of jigs includes: a drill guide jig used in a bone plate alignment phase.

* * * * *